US006350899B2

United States Patent
Herpich et al.

(10) Patent No.: US 6,350,899 B2
(45) Date of Patent: Feb. 26, 2002

(54) PROCESS FOR THE ESTERIFICATION OF UNSATURATED CARBOXYLIC ACIDS WITH UNSATURATED ALCOHOLS WITH AVOIDANCE OF BLACKENING AND PRECIPITATION

(75) Inventors: Rüdiger Herpich, Mannheim; Bernd Kray, Speyer; Roland Parg, Leverkusen; Erich Schmidt, Bürstadt; Stefan Schöpfer, Hockenheim; Iris Degen, Brühl, all of (DE)

(73) Assignee: Rhein Chemie Rheinau GmbH, Mannheim (DE)

( * ) Notice: Subject to any disclaimer, the term of this patent is extended or adjusted under 35 U.S.C. 154(b) by 0 days.

(21) Appl. No.: 09/790,351

(22) Filed: Feb. 21, 2001

(30) Foreign Application Priority Data

Feb. 24, 2000 (DE) .......................... 100 08 509

(51) Int. Cl.⁷ ............................................ C07C 69/007
(52) U.S. Cl. ....................................... 560/225; 560/218
(58) Field of Search ................................ 560/253, 218, 560/225

(56) References Cited

U.S. PATENT DOCUMENTS 6,001,913 A  * 12/1999 Thames ..................... 524/398

FOREIGN PATENT DOCUMENTS

DE        2913218     * 10/1980
JP        62121723    *  6/1987

* cited by examiner

*Primary Examiner*—Gary Geist
*Assistant Examiner*—Zachary C. Tucker
(74) *Attorney, Agent, or Firm*—Joseph C. Gil; Noland J. Cheung

(57) ABSTRACT

The present invention provides a process for the esterification of unsaturated carboxylic acids with unsaturated alcohols, which is characterized in that esterification is performed in the presence of sterically hindered phenols and partially esterified phosphoric acids.

The process according to the invention in particular avoids discoloration (blackening) of the resultant esterification products.

6 Claims, No Drawings

PROCESS FOR THE ESTERIFICATION OF UNSATURATED CARBOXYLIC ACIDS WITH UNSATURATED ALCOHOLS WITH AVOIDANCE OF BLACKENING AND PRECIPITATION

FIELD OF THE INVENTION

This invention relates to a process for the esterification of unsaturated carboxylic acids with unsaturated alcohols with avoidance of discoloration (blackening) and precipitation.

BACKGROUND OF THE INVENTION

The esterification of carboxylic acids with alcohols is known. In general, this reaction proceeds by mixing the acid and alcohol component in the presence of an acid catalyst and at elevated temperature.

The literature lists strong acids, such as sulfuric acid, hydrohalic acids and sulfonic acids for this purpose: author's collective, *Organikum*, 16$^{th}$ edition, VEB Deutscher Verlag der Wissenschaften, Berlin 1986, p. 402, H. Henecka, *Houben-Weyl, Methoden der organischen Chemie*, volume 8, Georg Thieme Verlag, Stuttgart 1952, pp. 516–526, H. Pielartzik, B. lrmisch-Pielartzik, T. Eicher, *Houben-Weyl, Methoden derorganischen Chemie*, volume E5/part 1, Georg Thieme Verlag, Stuttgart 1985, pp. 660–684 and W. Riemenschneider, *Ullmann's Enc. of Ind. Chemistry*, vol. A9, pp. 565–585. Disadvantages of using these catalysts in the esterification of unsaturated carboxylic acids with unsaturated alcohols are the black/brown coloration and optionally, precipitation, which occur during the reaction together with corrosion phenomena on metallic reaction containers. A further disadvantage of using these catalysts is that, after the reaction, they must be removed by washing or deactivated by neutralization. This is associated with higher plant costs or additional separation processes.

These disadvantages are also encountered when Lewis acids, such as boron trifluoride, are used as catalysts.

According to the above-stated literature, the quantity of the above-stated acids may be reduced by performing the reaction using the azeotropic esterification method. To this end, a solvent, which is capable of forming an azeotropic mixture with water, is added to the reaction mixture which contains a reduced quantity of catalyst. This process is also described in DE-A 2 913 218. The water of reaction is consequently removed and the course of the reaction is additionally accelerated. The disadvantage of this process is the use of solvents, which must be removed after the esterification and optionally disposed of.

According to the above-stated literature, esterification may also be performed using acidic ion exchangers. However, when applied to the esterification of mixtures of unsaturated carboxylic acids with unsaturated alcohols, blackening of the reaction mixture is unavoidable. A further disadvantage of this process is the inclusion of the additional process step of filtration or centrifugation in non-continuous production processes.

According to WO 92/00947, another possibility for avoiding blackening on esterification is to use additives having an oxidizing action, such as peroxides, hydroperoxides, hypochlorites.

Additives having a reducing action, such as hydrazine, hydroxylamine, sodium hydridoborate, are used for this purpose in JP-A 56 070 097 during the purification of unsaturated fatty acids by distillation.

According to U.S. Pat. No. 4,844,924, color stabilization is achieved by performing first oxidative, and then reductive bleaching.

According to DE-A 3 843 938, activated carbon is added during the esterification of unsaturated carboxylic acids to lighten/stabilize color. Aluminum oxide is used for the same purpose according to DE-A 40 19 778.

The disadvantage of the described methods of using oxidizing or reducing reagents or adsorbents is not only that, as described in the case of esterification with ion exchangers, an additional filtration or centrifugation operation is required, but also that the reaction products darken subsequently. Moreover, the added substances, some of which are highly reactive and toxic, must be removed or deactivated in order to allow the esters to be used in a wide range of applications. Using complex aluminum or boron hydrides may also result in the formation of flammable gases.

SUMMARY OF THE INVENTION

The object of the invention is to provide a process for the esterification of unsaturated carboxylic acids with unsaturated alcohols, by means of which light-colored products which are color-stable on storage may be produced. The process should also be applicable to mixtures of carboxylic acids and alcohols with unidentified accompanying substances, as occur as natural substances and in oil chemistry.

It has now been found that light-colored, color-stable reaction products are obtained by using partially esterified phosphoric acids together with sterically hindered phenols and introduction of inert gas.

The present invention accordingly provides a process for the esterification of unsaturated carboxylic acids with unsaturated alcohols, which is characterized in that esterification is performed in the presence of sterically hindered phenols and partially esterified phosphoric acids.

DETAILED DESCRIPTION OF THE INVENTION

Unsaturated alcohols which may be considered are mono- or polyunsaturated, linear or branched monoalcohols having 10 to 22 carbon atoms, preferably 10 to 18 carbon atoms. The following may be mentioned by way of example: decenol, undecenol, dodecenol, tridecenol, tetradecenol, pentadecenol, hexadecenol, heptadecenol, octadecenol, nonadecenol, eicosenol, heneicosenol, docosenol, decadienol, dodecadienol, tetradecadienol, hexadecadienol, octadecadienol, eicosadienol, docosadienol. Decenol, dodecenol, tetradecenol, hexadecenol, octadecenol are preferred. Decenol, dodecenol, palmitoleyl alcohol, oleyl alcohol are more preferred.

Unsaturated carboxylic acids, which may be used in the process according to the present invention are mono- or polyunsaturated, linear or branched monocarboxylic acids having 10 to 22 carbon atoms, preferably 14 to 18 carbon atoms.

Unsaturated carboxylic acids, which may be mentioned, by way of example, are: decenoic acid, undecenoic acid, dodecenoic acid, tridecenoic acid, tetradecenoic acid, pentadecenoic acid, hexadecenoic acid, heptadecenoic acid, octadecenoic acid, nonadecenoic acid, eicosenoic acid, heneicosenoic acid, docosenoic acid, decadienoic acid, dodecadienoic acid, tetradecadienoic acid, hexadecadienoic acid, octadecadienoic acid, octadecatrienoic acid, eicosatetraenoic acid. Tetradecenoic acid, hexadecenoic acid, octadecenoic acid, octadecadienoic acid and octadecatrienoic acid are preferred. Myristoleic acid, palmitoleic acid, oleic acid, linoleic acid and linolenic acid are more preferred.

Both the unsaturated alcohols and the unsaturated carboxylic acids may be used in the process according to the present invention individually and as mixtures with each other.

As mentioned above, the process according to the present invention is performed in the presence of partially esterified phosphoric acids and in the presence of sterically hindered phenols.

Partially esterified phosphoric acids which may be considered are phosphoric acid mono- and diesters having alkyl residues which comprise 1 to 10, preferably 1 to 8 carbon atoms in a linear, branched or cyclic arrangement. Examples which may be mentioned of partially esterified phosphoric acids usable in the process according to the present invention are: phosphoric acid dioctyl ester, phosphoric acid dihexyl ester, phosphoric acid dibutyl ester, phosphoric acid monooctyl ester, phosphoric acid monohexyl ester, phosphoric acid monobutyl ester. Phosphoric acid dioctyl ester, phosphoric acid dihexyl ester, phosphoric acid monooctyl ester, phosphoric acid monohexyl ester are preferred. Mixtures of phosphoric acid di-(2-ethylhexyl) ester, phosphoric acid mono(2-ethylhexyl) ester, phosphoric acid di-n-hexyl ester, phosphoric acid mono-n-hexyl ester in any desired mixture ratio are more preferred.

Phenols, which may be used as sterically hindered phenols in the process according to the present invention are those which are based on mononuclear or polynuclear, preferably mono- to tetranuclear phenols having at least two substituents, preferably 3 substituents, two substituents of which are in ortho position relative to the OH groups and which each comprise 1 to 80, preferably 1 to 60 carbon atoms, and contain up to 18, preferably up to 12 oxygen atoms.

Examples of these phenols are: 2,6-di-tert.-butyl-4-methylphenol, 2,6-di-tert.-butyl-4-ethylphenol, 2,6-di-tert.-butyl-4-nonylphenol, 2,6-di-tert.-butyl-4-sec.-butylphenol, 2,6-dibenzyl-4methylphenol, 3-(3,5-di-tert.-butyl-4hydroxyphenyl)propanoic acid methyl ester, 3-(3,5-di-tert.-butyl-4 hydroxyphenyl)propanoic acid octadecyl ester, 2,2'-methylenebis(6-tert.-butyl- 4-methylphenol), 2,2'-methylenebis(6-tert.-butyl-4-ethylphenol), 2,2'-methylenebis (4-methyl-6-cyclohexylphenol), 4,4'-methylenebis(2,6-di-tert.butylphenol), 2,2'-ethylidenebis(4,6-di-tert.-butylphenol), 4,4'-butylidene-bis (6-tert.-butyl-3-methylphenol), 2,2'-isobutylidenebis(4,6-dimethylphenol), 1,3,5-trimethyl-2,4,6-tris(3,5-di-tert.-butyl-4-hydroxybenzyl)-benzene, hexamethylenebis(3,5-di-tert.-butyl-4-hydroxyhydrocinnamate), pentaerythrityl tetrakis[3-(3,5-di-tert.-butyl-4-hydroxyphenyl)propionate], 1,3,5-trimethyl-2,4,6-tris(3,5-di-tert.-butyl-4-hydroxybenzyl) benzene. 2,6-Di-tert.-butyl-4-methylphenol, 2,2'-methylenebis(6-tert.-butyl-4-methylphenol), 2,2'-methylenebis(4-methyl-4-cyclohexylphenol), pentaerythrityl tetrakis[3-(3,5-di-tert.-butyl-4-hydroxyphenyl)propionate] and 1,3,5-trimethyl-2,4,6-tris(3, 5-di-tert.-butyl-4-hydroxybenzyl)benzene are preferred. 2,6-Di-tert.-butyl-4-methylphenol, pentaerythrityl tetrakis[3-(3, 5-di-tert.-butyl-4-hydroxyphenyl)propionate] and 1,3,5-trimethyl-2,4,6-tris (3,5-di-tert.-butyl-4-hydroxybenzyl) benzene are most preferred.

Both the sterically hindered phenols and the partially esterified phosphoric acids may be used alone or as mixtures with each other. The particular mixture ratio may readily be adjusted by appropriate preliminary testing and is, in particular, determined by the alcohols and acids used.

The partially esterified phosphoric acids are generally used in quantities of 0.01 to 5 wt. %, relative to the total quantity of alcohol and carboxylic acid. Quantities of 0.1 to 1.5 wt. % are preferred. Quantities of 0.3 to 1.0 wt. % are most preferred.

The quantity of sterically hindered phenols is generally 0.01 to 3 wt. %, relative to the total quantity of alcohols and carboxylic acids.

Quantities of 0.05 to 1.0 wt. % are preferred. Quantities of 0.08 to 0.5 wt. % are more preferred.

In the process according to the present invention, the ratio of partially esterified phosphoric acids to sterically hindered phenols is conventionally (50-0.1):1, preferably (10-1):1.

The unsaturated carboxylic acids and the alcohols are used according to the present invention in a molar ratio of 1:(2-0.5), preferably of 1:(1.1-0.9).

In a preferred embodiment of the process according to the present invention, esterification is performed with introduction of inert gas, such as nitrogen or argon. The quantity of inert gas is not critical and may readily be determined by appropriate preliminary testing.

In a preferred embodiment, the process according to the present invention is performed at temperatures in the range from 130 to 200° C., preferably, at temperatures in the range from 150 to 180° C. The unsaturated monocarboxylic acids and unsaturated alcohols are reacted with the partially esterified phosphoric acids and sterically hindered phenols without addition of solvents or entraining agents with the introduction of inert gas. The resultant water of reaction is removed with the stream of inert gas in the conventional manner, for example by connecting a Liebig condenser downstream.

EXAMPLES

Unless otherwise stated, the percentage values relate to percentage areas in the particular gas chromatogram of the alcohol or carboxylic acid component.

Comparative Example 1

100.0 g of an alcohol component consisting of: 75 wt. % oleyl alcohol, 25 wt. % hexadecyl alcohol and 105.6 g of an acid component consisting of: 70% oleic acid, 8.3% linoleic acid, 5.3% palmitoleic acid, 16.4% of acids with a chain length of C14–C18 are mixed with 0.6 g of para-toluenesulfonic acid and heated until the acid value falls to below 10 mg of KOH/g.

Blackening of the reaction batch and precipitation. Hess-Ivess color index of the mixture (Hess-Ivess color index: DKG method no.: F010.1, from Deutsche Gesellschaft für wissenschaftliche und angewandte Kosmetik [German society for scientific and applied cosmetics])

| before the reaction: 8.8 | after the reaction: 300.2. |
|---|---|

Comparative Example 2

70.0 g of an alcohol component consisting of: 93% oleyl alcohol, 7% alcohols with a chain length of C12–C22 and 75.0 g of an acid component consisting of: 70% oleic acid, 8.3% linoleic acid, 5.3% palmitoleic acid, 16.4% of acids with a chain length of C14–C18 are mixed with 2.6 g of ion exchanger Deloxan® ASP 1/9 (Degussa, propyl(3-sulfonic acid)siloxane/silicon dioxide copolycondensation product) and heated until the acid value falls to below 20 mg of KOH/g.

Darkening of the reaction batch.
Hess-Ivess color index of the mixture

| before the reaction: 8.8 | after the reaction: 116.4. |
|---|---|

Comparative Example 3

70.0 g of an alcohol component consisting of: 93% oleyl alcohol, 7% alcohols with a chain length of C12–C22 and 75.0 g of an acid component consisting of: 70% oleic acid, 8.3% linoleic acid, 5.3% palmitoleic acid, 16.4% of acids with a chain length of C14–C18 are mixed with 0.5 g of phosphoric acid and heated until the acid value falls to below 10 mg of KOH/g.
Darkening of the reaction batch, formation of brown flocs.
Hess-Ivess color index of the mixture

| before the reaction: 0.0 | after the reaction: 97.5. |
|---|---|

Example 4

70.0 g of an alcohol component consisting of: 93% oleyl alcohol, 7% alcohols with a chain length of C12–C22 and 75.0 g of an acid component consisting of: 70% oleic acid, 8.3% linoleic acid, 5.3% palmitoleic acid, 16.4% of acids with a chain length of C14–C18 are mixed with 0.73 g of phosphoric acid di-(2-ethylhexyl) ester/phosphoric acid mono-2-ethylhexyl mixture and 0.15 g of 2,6-di-tert.-butyl-4-methylphenol and heated until the acid value falls to below 10 mg of KOH/g.
The ester mixture is in the form of a clear, pale yellow liquid.
Hess-Ivess color index of the mixture

| before the reaction: 8.8 | after the reaction (stability time 1 year): 14.2. |
|---|---|

Example 5

65.8 g of an alcohol component consisting of: 93% oleyl alcohol, 7% alcohols with a chain length of C12–C22 and 71.1 g of an acid component consisting of: 35 wt. % oleic acid, 55 wt. % linoleic acid and 10 wt. % octadecatrienoic acid are mixed with 0.69 g of phosphoric acid di-(2-ethylhexyl) ester/phosphoric acid mono-2-ethylhexyl ester mixture and 0.27 g of pentaerythrityl tetrakis[3-(3,5-di-tert.-butyl-4-hydroxyphenyl)-propionate] and heated until the acid value falls to below 10 mg of KOH/g.
The ester mixture is in the form of a clear, yellow liquid.
Hess-Ivess color index of the mixture

| before the reaction: 2.1 | after the reaction: 39.7. |
|---|---|

Example 6

74.8 g of an alcohol component consisting of: 93% oleyl alcohol, 7% alcohols with a chain length of C12–C22 and 80 g of an acid component consisting of: 23 wt. % oleic acid, 10 wt. % palmitic acid, 53 wt. % linoleic acid, 9 wt. % linolenic acid are mixed with 0.4 g of phosphoric acid di-(2-ethylhexyl) ester/phosphoric acid mono-2-ethylhexyl ester mixture and 0.31 g of 1,3,5-trimethyl-2,4,6-tris(3,5-di-tert.-butyl-4 hydroxybenzyl)benzene and heated until the acid value falls to below 10 mg of KOH/g.
The ester mixture is in the form of a clear, orange liquid.
Hess-Ivess color index of the mixture

| before the reaction: 0.2 | after the reaction: 61.7. |
|---|---|

Example 7

80.0 g of an alcohol component consisting of: 93% oleyl alcohol, 7% alcohols with a chain length of C12–C22 and 80 g of an acid component consisting of: 70% oleic acid, 8.3% linoleic acid, 5.3% palmitoleic acid, 16.4% acids with a chain length of C14–C18 are mixed with 0.4 g of phosphoric acid di-(2-ethylhexyl) ester/phosphoric acid mono-2-ethylhexyl ester mixture and 0.15 g of pentaerythrityl tetrakis [3-(3,5-ditert.-butyl-4-hydroxyphenyl)propionate] and heated until the acid value falls to below 10 mg of KOH/g.
The ester mixture is in the form of a clear, orange liquid.
Hess-Ivess color index of the mixture

| before the reaction: 0.0 | after the reaction: 61.7. |
|---|---|

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the esterification of unsaturated carboxylic acids with unsaturated alcohols comprising the step of performing esterification in the presence of sterically hindered phenols and partially esterified phosphoric acids.

2. A process according to claim 1, wherein esterification is performed with introduction of inert gas.

3. A process according to claim 1, wherein esterification is performed in the presence of 0.1 to 3 wt. % of sterically hindered phenols, relative to the total quantity of alcohol and carboxylic acid.

4. A process according to claim 1, wherein esterification is performed in the presence of 0.01 to 5 wt. % of partially esterified phosphoric acids, relative to the total quantity of alcohol and carboxylic acid.

5. A process according to claim 1, wherein the unsaturated carboxylic acids and the unsaturated alcohols are used in a molar ratio of 1:2–0.5.

6. A process according to claim 1, wherein the ratio of partially esterified phosphoric acids to sterically hindered phenols is 50-0.1:1.

* * * * *